United States Patent [19]
Rusk et al.

[11] Patent Number: 5,681,280
[45] Date of Patent: Oct. 28, 1997

[54] CATHETER CONTROL SYSTEM

[75] Inventors: Scott J. Rusk, Sun City; Eugene J. Jung, Jr., San Diego; Wade A. Bowe, Temecula; John A. Simpson, Carlsbad, all of Calif.

[73] Assignee: Heart Rhythm Technologies, Inc., Temecula, Calif.

[21] Appl. No.: 434,003

[22] Filed: May 2, 1995

[51] Int. Cl.⁶ ............................................. A61M 25/092
[52] U.S. Cl. ............................................. 604/95; 604/105
[58] Field of Search ..................... 604/95, 264, 104, 604/105, 101, 106, 114; 600/139, 145, 146, 150; 128/772; 607/122

[56] References Cited

U.S. PATENT DOCUMENTS

| | | |
|---|---|---|
| Re. 34,502 | 1/1994 | Webster, Jr. .............. 607/125 |
| 3,452,740 | 7/1969 | Muller . |
| 3,470,876 | 10/1969 | Barchilon . |
| 3,521,620 | 7/1970 | Cook . |
| 3,552,384 | 1/1971 | Peirie et al. . |
| 3,605,725 | 9/1971 | Bentov . |
| 3,610,231 | 10/1971 | Takahashi et al. . |
| 4,207,873 | 6/1980 | Kruy . |
| 4,483,326 | 11/1984 | Yamaka et al. . |
| 4,503,842 | 3/1985 | Takayama . |
| 4,898,577 | 2/1990 | Badger et al. .............. 604/53 |
| 4,940,062 | 7/1990 | Hampton et al. ............ 128/772 |
| 5,030,204 | 7/1991 | Badger et al. ............ 604/95 |
| 5,125,896 | 6/1992 | Hojeibane .................. 604/95 |
| 5,170,787 | 12/1992 | Lindegren . |
| 5,181,514 | 1/1993 | Solomon et al. . |
| 5,185,004 | 2/1993 | Lashinski ................. 604/95 |
| 5,190,050 | 3/1993 | Nitzsche .................. 128/772 |
| 5,195,968 | 3/1993 | Lundquist et al. ......... 604/95 |
| 5,228,441 | 7/1993 | Lundquist . |
| 5,242,430 | 9/1993 | Arenas et al. ............ 604/280 |
| 5,242,441 | 9/1993 | Avitall ................... 606/41 |
| 5,254,088 | 10/1993 | Lundquist et al. ......... 604/95 |
| 5,255,668 | 10/1993 | Umeda . |
| 5,255,684 | 10/1993 | Rello .................... 128/662.06 |
| 5,257,451 | 11/1993 | Edwards et al. . |
| 5,263,493 | 11/1993 | Avitall .................. 607/122 |
| 5,273,535 | 12/1993 | Edwards et al. .......... 604/95 |
| 5,281,217 | 1/1994 | Edwards et al. .......... 606/41 |
| 5,284,128 | 2/1994 | Hart ..................... 128/4 |
| 5,318,525 | 6/1994 | West et al. ............. 604/95 |
| 5,327,905 | 7/1994 | Avitall ................. 128/772 |
| 5,330,466 | 7/1994 | Imran ................... 606/13 |
| 5,346,504 | 9/1994 | Ortiz et al. ............ 606/192 |
| 5,354,297 | 10/1994 | Avitall ................. 606/45 |
| 5,358,479 | 10/1994 | Wilson .................. 604/95 |
| 5,363,861 | 11/1994 | Edwards et al. ......... 128/772 |
| 5,368,564 | 11/1994 | Savage .................. 604/95 |
| 5,370,678 | 12/1994 | Edwards et al. ......... 607/101 |
| 5,383,852 | 1/1995 | Stevens-Wright ......... 604/95 |
| 5,383,923 | 1/1995 | Webster, Jr. ........... 607/125 |
| 5,385,148 | 1/1995 | Lesh et al. ............ 128/662.06 |
| 5,395,327 | 3/1995 | Lundquist et al. ....... 604/95 |
| 5,402,793 | 4/1995 | Gruner et al. .......... 128/660.1 |

(List continued on next page.)

*Primary Examiner*—Michael Powell Buiz
*Assistant Examiner*—A. T. Nguyen
*Attorney, Agent, or Firm*—Fulwider Patton Lee & Utecht, LLP

[57] ABSTRACT

A steerable catheter comprising a resilient deflectable body member having an expandable electrode array at the distal end thereof, and a manipulation handle attached to the proximal end of the body member, the handle including an array deployment device. A mandrel is movable through the shaft of the catheter by control movements at the handle to deploy the array or collapse the array as selected. A displacement compensation system is operatively connected to the mandrel such that when the array is expanded, the compensation system biases the mandrel so keep the array expanded, even during instances of deflection of the distal end. Similarly, the displacement compensation system biases the mandrel to keep the array collapsed when that configuration is selected, even during instances of straightening of the catheter. The displacement compensation system also compensates for overturning the control device in the handle to protect the array and deployment systems.

22 Claims, 8 Drawing Sheets

U.S. PATENT DOCUMENTS

| | | | |
|---|---|---|---|
| 5,403,297 | 4/1995 | Imran | 604/281 |
| 5,421,832 | 6/1995 | Lefebrve | 604/53 |
| 5,431,168 | 7/1995 | Webster, Jr. | |
| 5,441,483 | 8/1995 | Avitall | 604/95 |
| 5,465,716 | 11/1995 | Avitall | 128/642 |
| 5,471,982 | 12/1995 | Edwards et al. | 128/642 |
| 5,476,495 | 12/1995 | Kordis et al. | 607/122 |
| 5,531,686 | 7/1996 | Lundquist et al. | 604/95 |
| 5,531,687 | 7/1996 | Snoke et al. | 604/95 |
| 5,549,542 | 8/1996 | Kovalcheck | 600/146 |

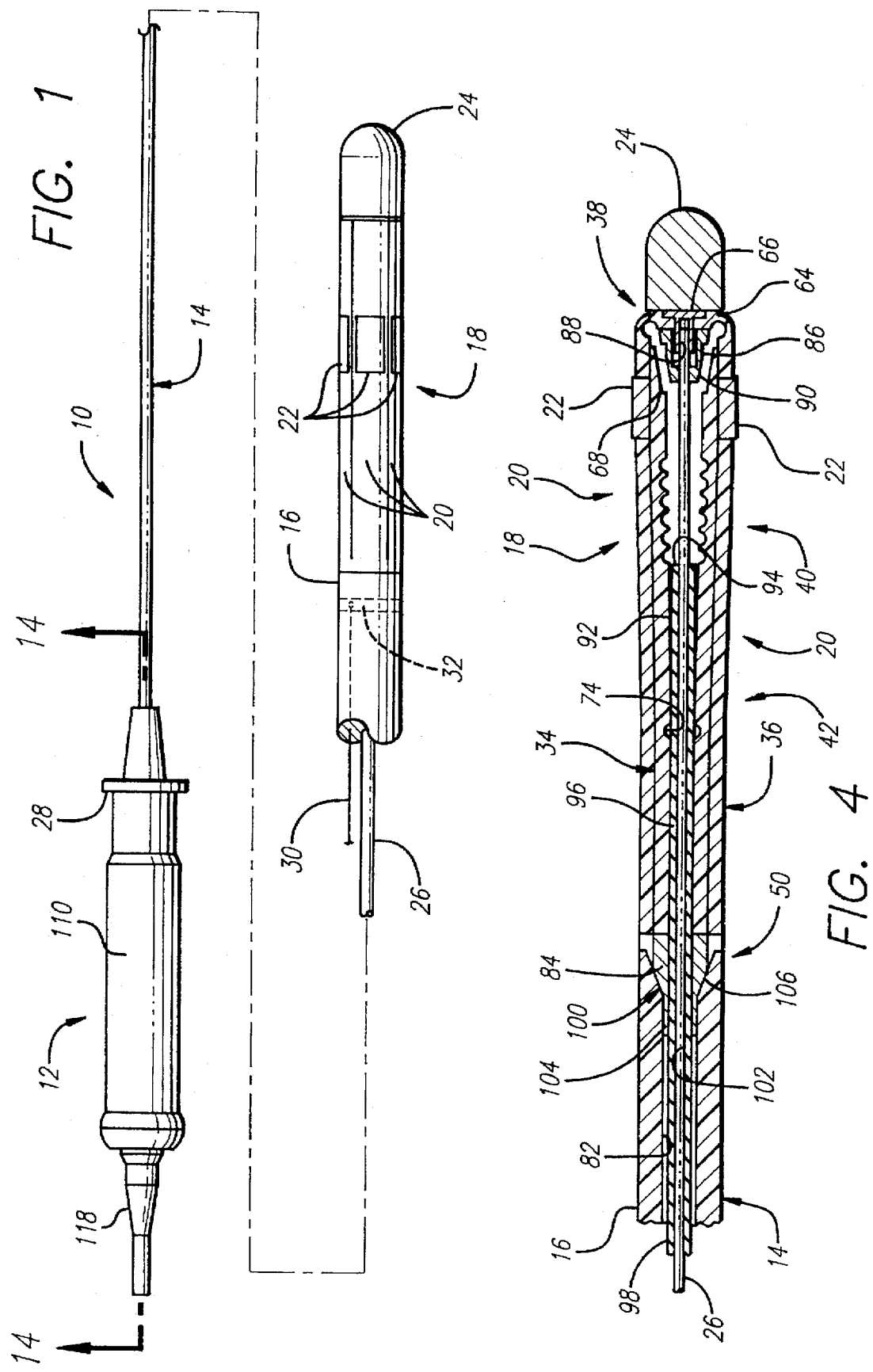

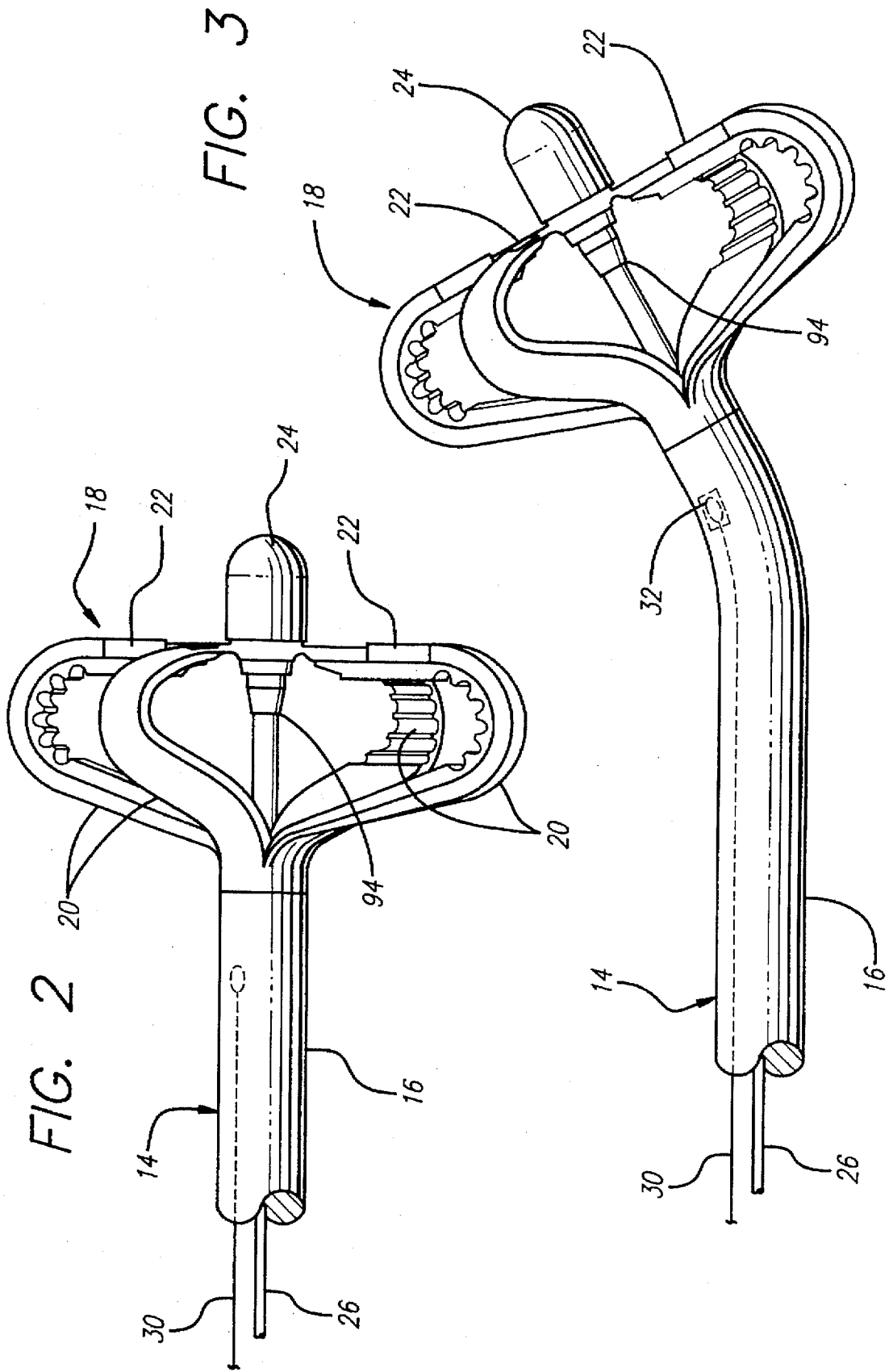

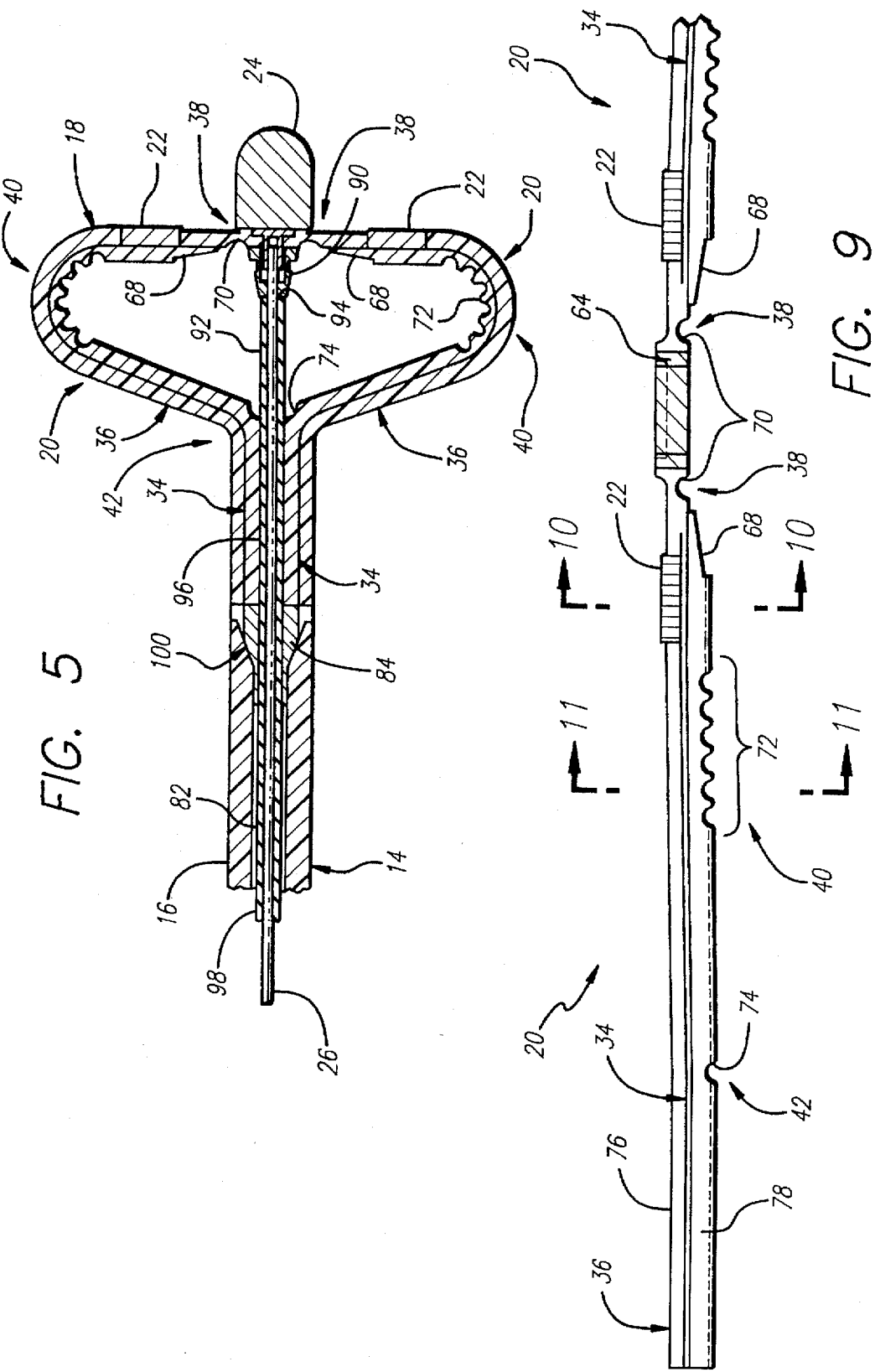

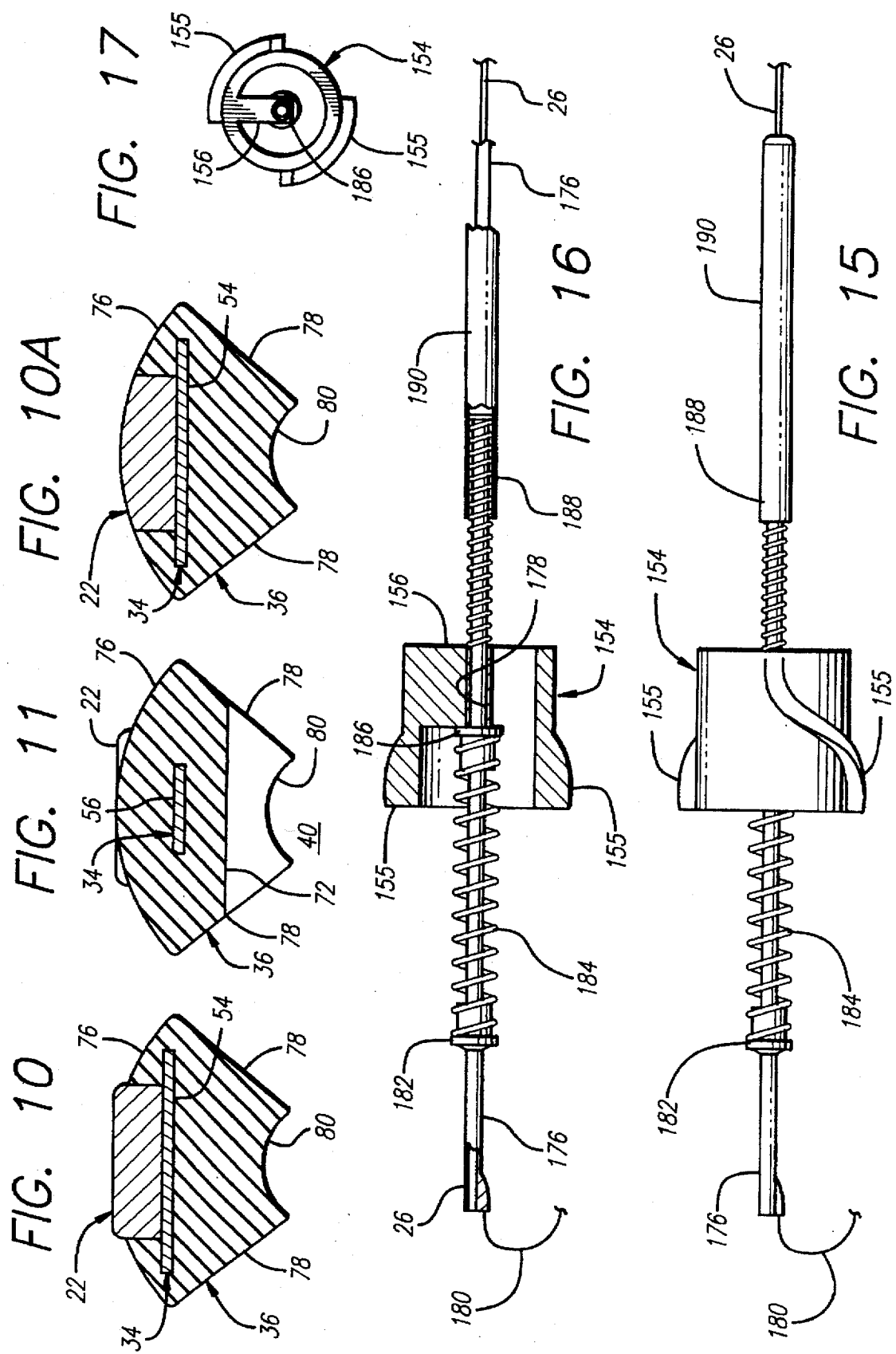

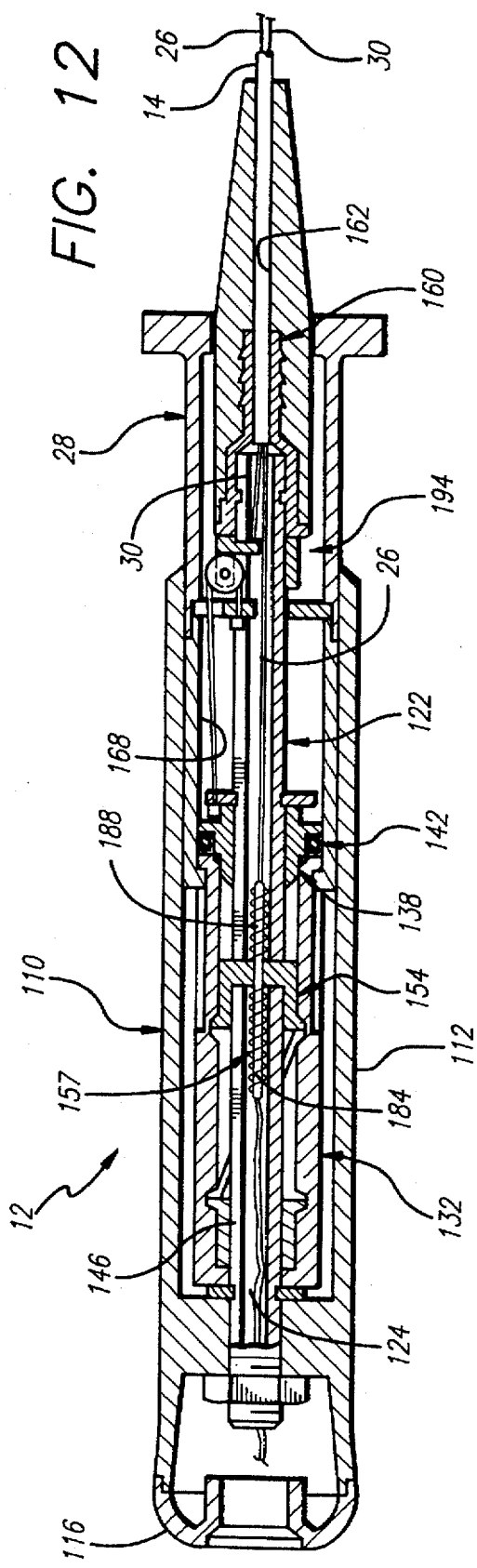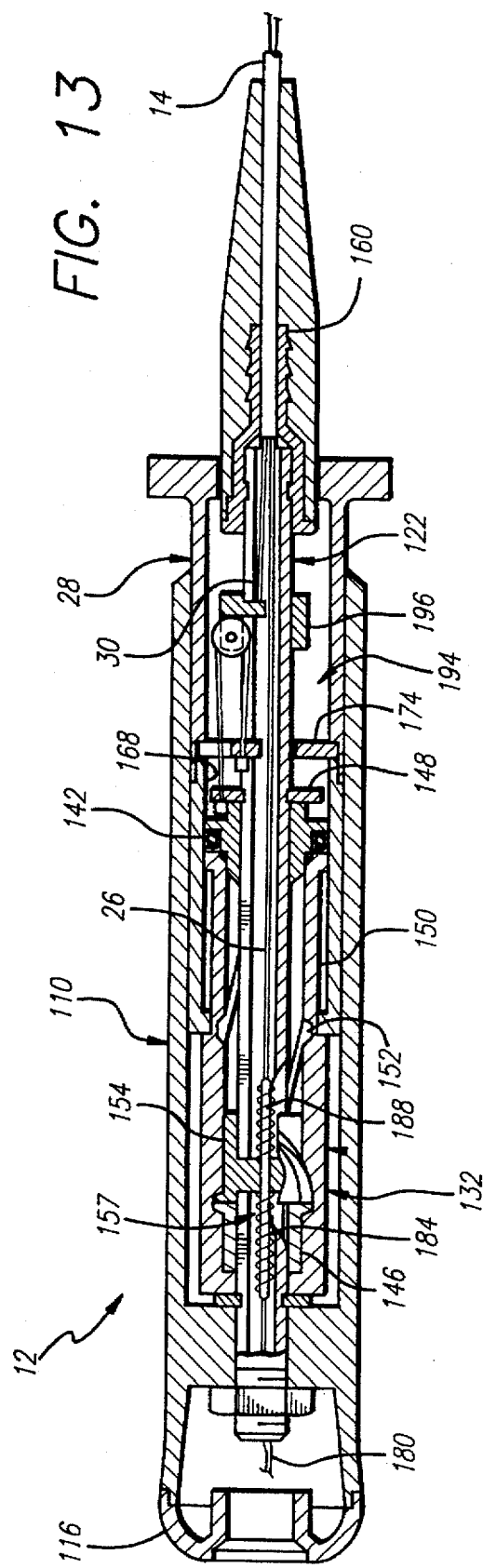

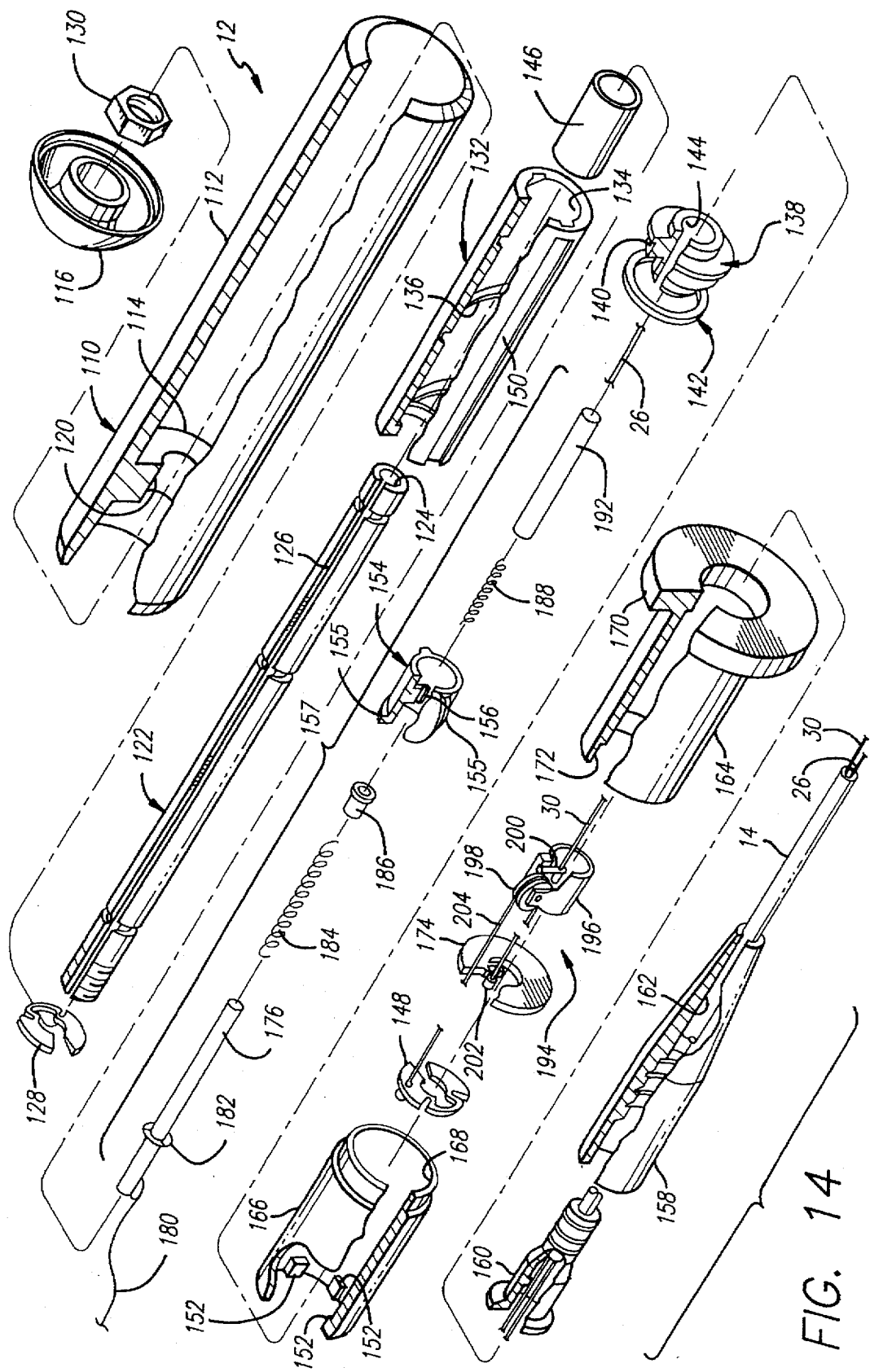

CATHETER CONTROL SYSTEM

BACKGROUND

The invention relates generally to catheters, and more particularly, to control mechanism usable in controlling the configuration of a catheter.

The heart beat in a healthy human is controlled by the sinoatrial node ("S-A node") located in the wall of the right atrium. The S-A node generates electrical signal potentials that are transmitted through pathways of conductive heart tissue in the artium to the atrioventricular node ("A-V node") which in turn transmits the electrical signals throughout the ventricle by means of the His and Purkinje conductive tissues. Improper growth of or damage to the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as cardiac arrhythmia.

Electrophysiological ablation in a procedure often successful in terminating cardiac arrhythmia. This procedure involves applying sufficient energy to the interfering tissue to ablate that tissue thus removing the irregular signal pathway. However, before an ablation procedure can be carried out, the interfering tissue must first be located.

One location technique involves an electrophysiological mapping procedure whereby the electrical signals emanating from the conductive endocardial tissues are systematically monitored and a map is created of those signals. By analyzing that map, the interfering electrical pathway can be identified. A conventional method for mapping the electrical signals from conductive heart tissue is to percutaneously introduce an electrophysiology ("EP") catheter having mapping electrodes mounted on its distal extremity. The catheter is maneuvered to place those electrodes in contact with or in close proximity to the endocardium of the patient's heart. By monitoring the electrical signals at the endocardium, aberrant conductive tissue sites responsible for the arrhythmia can be pinpointed.

Once the origination point for the arrhythmia is located in the tissue, the physician may use an ablation procedure to destroy the tissue causing the arrhythmia in an attempt to remove the electrical signal irregularities and restore normal heart beat or at least improve the heart beat. Successful ablation of the conductive tissue at the arrhythmia initiation site usually terminates the arrhythmia or at least moderates the heart rhythm to acceptable levels.

As the EP catheter is introduced, the catheter is directed through the irregularly shaped path defined by the blood vessel and branch vessels until the distal end of the catheter reaches the heart chamber. The diameter of the catheter must be relatively small so that the catheter may be moved through the relatively small diameter blood vessels to the heart. Once the distal end of the catheter is at the desired location within the heart, EP mapping and ablation procedures may commence.

It has been found that if the plurality of mapping electrodes are located in a spaced-apart planar grid, the electrical signals emanating from the endocardium of the heart may be more efficiently and accurately mapped using vector analysis to pinpoint arrhythmias. However, such a configuration increases the size of the catheter substantially and inhibits percutaneous introduction of the catheter through the vascular system. Therefore, some EP catheters are provided with an expandable/collapsible electrode array located at their distal ends. Once positioned within the intracardial dial volume of the heart, the array can be deployed wherein the mapping electrodes are positioned so that they are spaced outwardly relative to one another in the planar-type array.

To expand the electrode array to its completely deployed state, a deployment mandrel is located in the catheter lumen, connected at its distal end to the electrode array, and connected at its proximal end to a deployment control device. The deployment control device is included in a catheter manipulation handle at the proximal end of the catheter tube. The deployment control device may be manually operated to pull the mandrel and the center of the array in a proximal direction relative to the catheter tube to expand the electrode array to its fully deployed position at the end of the catheter. The catheter may then be used for the mapping/ablation procedure.

To maneuver the deployed array as desired to reach target tissue, the steerable catheter may incorporate a deflection control line to control the deflection of the distal tip. Pulling the proximal end of the control line at the manipulation handle causes the distal tip of the catheter to deflect in one direction so that the tip may be directed through selected blood vessels or put into the desired location in the heart. Such a system is shown in U.S. Pat. No. 5,364,352 to Cimino et al.

Once the EP catheter has been directed to the heart, the deployment mandrel may be pulled to deploy the electrode array. The deflection control line may be then operated to adjust the curvature at the end of the catheter to direct or steer the electrode array toward selected tissue sites. The curvature and position of the distal end of the catheter may have to be finely adjusted many times in order to properly position the array for complete and comprehensive monitoring of the electrical signals emanating from the conductive heart tissue to effectively map and detect arrhythmatic points of origin.

In a steerable EP catheter, for example, it has been found that deflecting the distal tip of the catheter to a bent shape causes the outer catheter tube to undergo some compression and actually shorten in length somewhat. However, devices internal to the catheter tube and not connected directly to it do not change in length, or at least do not change in length as much, when the distal tip of the catheter is deflected. They thus become longer relative to the outer catheter tube. This change in relative lengths can affect the deployment of an electrode array that is mounted to the outer catheter tube and controlled by an internal mandrel. When the electrode array has been fully deployed while the catheter outer tube was straight, the array may collapse somewhat when the catheter is deflected. This partial collapse is undesirable as it may affect the mapping procedure. The electrodes are no longer at their expected positions. If the array contracts somewhat, electrical impulse detection from the endocardial wall may be somewhat compromised, reducing mapping effectiveness. Thus, the physician may have to make further adjustments of the deployment control mandrel to assure that the array is fully deployed, if the need for this can be detected. In many cases in a percutaneous procedure, it is difficult to determine the exact configuration details of an array. Fluoroscopy may not provide the level of detail needed by the physician to note that partial collapse of the array has occurred.

In another undesirable situation, a relative lengthening of the outer tube of the catheter may cause the array to partially deploy. Such an event could occur when the array is collapsed for movement or withdrawal of the catheter while the catheter distal end is in a deflected position. Should the catheter then be straightened, the outer tube may lengthen in relation to the internal mandrel thus causing the mandrel to move proximally, in relation to the outer tube, thereby pulling the array to a partially deployed position. Withdrawing the catheter through the blood vessels of the patient may be made more difficult in this situation. Once again, this situation may be difficult to detect by the physician.

In addition, when the electrode array is in its undeployed state and is being directed through the vascular system to the heart during the advancement procedure, longitudinal compression of the distal end of the catheter when in a deflected position can cause the distal end of the deployment mandrel to extend or be displaced relative to the catheter tube. This extension may result in the mandrel applying pressure on the center of the already collapsed array exerting an undue force on the electrode array which may stretch the components of the array resulting in damage.

Hence, those skilled in the art have recognized the need for a catheter that maintains the relative distal positions of the outer and internal components during deflection of the distal end of the catheter. Such a need has been particularly recognized in the case of a catheter having an expandable array mounted to the distal tip of a catheter. More particularly, a need exists for a displacement compensation device for use with steerable EP catheters having expandable electrode probe arrays at their distal ends. Such a displacement compensation device should maintain the relative alignment of the catheter components during deflection of the catheter during navigation of the catheter through the blood vessels of the patient and in operation of the catheter at the treatment site in the patient. The present invention fulfills these needs and others.

SUMMARY OF THE INVENTION

Briefly and in general terms, the present invention is directed to a biasing system that controls the position of a control device disposed within a catheter, the catheter having proximal and distal ends with the control device being movable longitudinally in the catheter. More particularly, the biasing system provides a bias force to urge the movable control device to maintain a selected relative position with the catheter.

In a more detailed aspect, the catheter includes a body member, the proximal end of which is attached to a manipulation handle that includes a linearly movable first positioning element. The control device is disposed within the body member and is connected to the first positioning element through the biasing system such that movement of the first positioning element is communicated to the control device and results in movement of the control device within the catheter body. When the first positioning element is moved to place the control device in a selected position in the body member of the catheter, the biasing system provides biasing force to the control device to maintain the control device in that selected position.

In yet a further detailed aspect, the biasing system applies biasing force to the control device to maintain the control device in a fixed position relative to the distal end of the body member of the catheter. Such relative position is maintained throughout the movement range of the distal end of the catheter body member.

In one aspect of the invention, the catheter includes an operation member mounted at the distal end of the body member. The control device is connected to the operation member and controls its operation through the relative position of the control device in the body member. The body member further includes a stop surface mounted at the distal end of the body member that restricts the operation device from proximal movement past the stop surface. When the first position element is moved in a proximal direction thereby moving the control device proximally and the operation device against the stop surface, the biasing system provides enough biasing force to the control device to maintain the operation device at the stop surface throughout the range of deflection of the distal end of the body member.

In a particular aspect of the invention, the biasing member comprises a helical coil spring mounted between the first positioning device and the control device to transmit movement of the positioning device to the control device and bias the control device in a predetermined direction. In a more detailed aspect, the coil spring and first positioning device are arranged in relation to the control device so that the coil spring is in compression when the operation device is in contact with stop surface to urge the operation device further into contact with the stop surface. In an alternative arrangement, the helical coil spring is arranged so that it is in tension when the operation device is in contact with the stop surface to urge the operation device further into contact with the stop surface.

In a further detailed aspect, the biasing system comprises a pair of springs disposed on opposite ends of the first positioning element. One end of each of the respective springs is in confronting alignment with opposite ends of the first positioning element and the opposite ends of the respective springs are mounted to spring engagement rings on the control device. More particularly, the two springs are slidably disposed over the control device, and the control device is formed with a pair of spaced-apart stop rings disposed on opposite sides of the first positioning element, against which the second ends of the respective springs abut.

In yet a further detailed aspect, the operation device comprises an expandable array of electrodes with the control device connected to the array to control its expansion and contraction. The array is mounted to the distal end of the body member and the position of the control device in relation to that distal end controls the expansion and contraction of the array. The stop surface restricts the expansion of the array to a full deployment position.

In a further aspect, the array includes an ablation electrode to which the first positioning device is electrically connected. The first positioning device is formed of electrically conductive material and is electrically connected to the proximal end of the catheter. The first positioning device provides an electrical path for the ablation electrode as well as controlling the expansion and contraction of the array in relation to the body member.

In a further particular aspect of the invention, the catheter further comprises a second control device connected between the proximal and distal ends of the catheter that controls the deflection of the distal end of the catheter. The biasing system is arranged to maintain the relative position of the first control device in a selected position to the distal end of the body member throughout the full range of movement of deflection of the second control device.

In another aspect, the proximal end of the catheter includes a rotatable element connected to the first positioning member such that rotation of the rotatable element causes linear motion of the first positioning member.

Other aspects and advantages of the invention will become apparent from the following detailed description and accompanying drawings, illustrating by way of example the features of the invention.

BRIEF DESCRIPTION OF THE DRAWINGS

FIG. 1 is a side view of an electrophysiological catheter embodying features of the invention, and illustrating the distal end thereof having an expandable electrode array in its collapsed or unexpanded configuration;

FIG. 2 is a side view of the distal portion of the electrophysiological catheter shown in FIG. 1 illustrating the expandable electrode array in its expanded configuration;

FIG. 3 is a side view of the distal portion of the electrophysiological catheter shown in FIG. 2 illustrating the expanded electrode array with the distal end of the catheter in a deflected configuration;

FIG. 4 is an enlarged partial sectional side view of the distal portion of the catheter shown in FIG. 1;

FIG. 5 is a partial sectional side view of the distal portion of the catheter shown in FIG. 2;

FIG. 9 is an enlarged, partially broken, partially sectional and rotated side view of the array of FIG. 8;

FIG. 10 is an enlarged cross sectional view of one segment of the array taken along lines 10—10 of FIG. 9, and depicting a sensing electrode mounted thereon in one configuration;

FIG. 10A is an enlarged cross sectional view of one segment, similar to that shown in FIG. 10, but illustrating the sensing electrode having a different shape;

FIG. 11 is an enlarged cross sectional view of one segment of the array taken along lines 11—11 of FIG. 9; and FIG. 12 is an enlarged side view, partially in section, taken along lines 12—12 of FIG. 1 of a manipulation handle secured to the proximal end of the catheter including an array deployment control device in a distal position to collapse the array, and including a deflection control device in its non-operative position (catheter not deflected), and further including a displacement compensation device in accordance with the invention;

FIG. 13 is partially sectional side view of the manipulation handle shown in FIG. 12 including an array deployment control device in its operative position to expand the array, and including a deflection control device in its operative position to deflect the distal end of the catheter;

FIG. 14 is an exploded perspective view, partially in section, of the manipulation handle shown in FIGS. 12 and 13;

FIG. 15 is an enlarged side view of the displacement compensation device shown in FIGS. 12 and 13;

FIG. 16 is an side view, partially in section, of the displacement compensation device shown in FIG. 17; and FIG. 17 is an end view of the displacement compensation device shown in FIGS. 15 and 16.

DETAILED DESCRIPTION OF THE PREFERRED EMBODIMENTS

Figure 8:
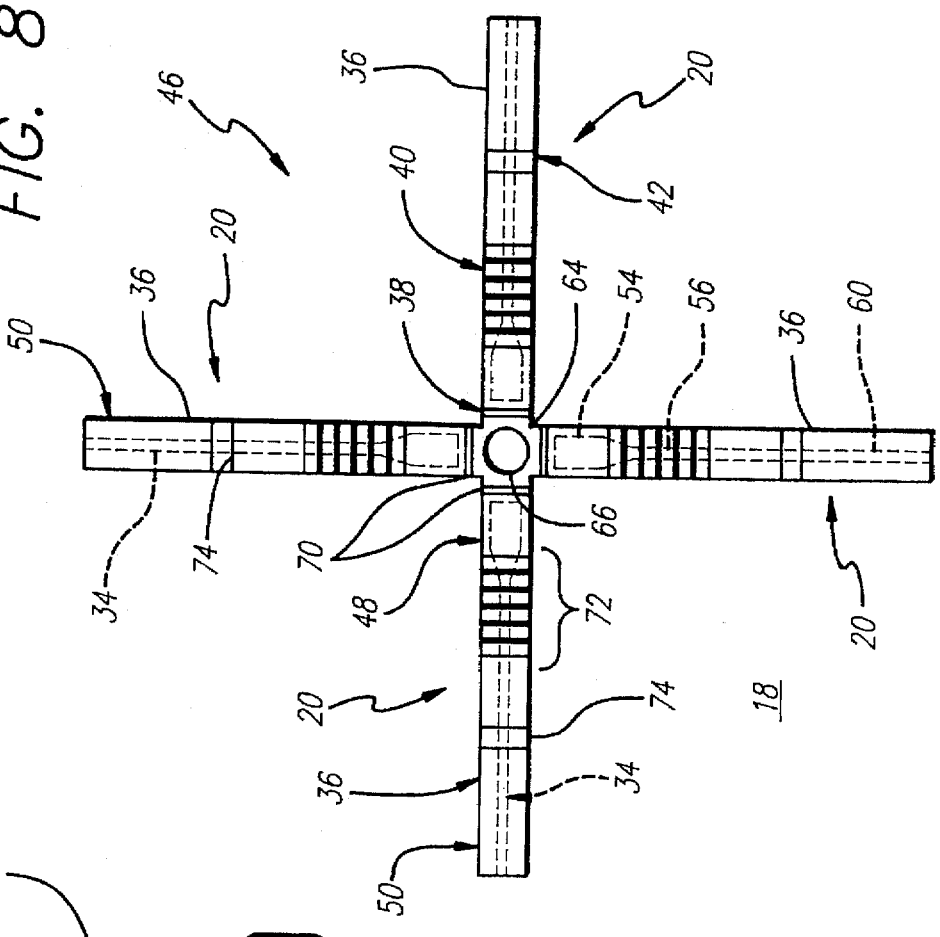
FIG. 8 is a enlarged bottom view of the core members of the array encapsulated in polymeric casings and trimmed from the frame shown in FIG. 6 to form a plurality of array segments.
Figure 6:
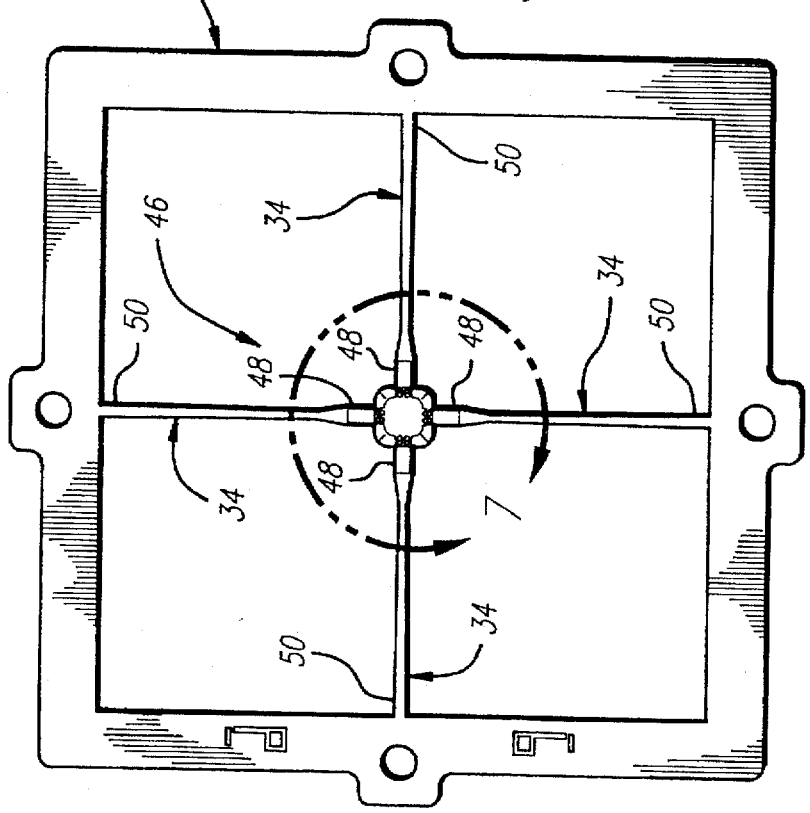
FIG. 6 is a top view of a metallic frame used during fabrication of the expandable array including a plurality of core members of the expandable array.

In the following description, like reference numerals will be used to designate like or corresponding elements among the several figures of the drawings. Referring now to the drawings and particularly to FIG. 1 there is shown a catheter 10 usable for electrophysiological procedures and embodying features of the invention. Briefly, the catheter 10 includes a manipulation handle 12, an elongated catheter shaft or body member 14, an expandable electrode array 18 located at the distal end 16, a deployment control device 26, and a body member deflection control device 30.

The expandable electrode array 18 includes a plurality of peripheral elongated segments 20 with each segment including an exposed electrode 22 on its exterior, and a generally hemispherical tip electrode 24 at the distal tip of the array 18. The body member 14 has an inner lumen (not shown) that extends to the distal tip and that has disposed therein a plurality of electrical conductors that are electrically connected to the electrodes 22. In addition, the deployment control device 26 is slidably disposed within the inner lumen of the catheter body member 14 and preferably comprises an electrically conductive deployment mandrel 26 having its distal end not only electrically connected but also mechanically fastened to the tip electrode 24.

The plurality of distal end segments 20 are flexible and resilient and configured in a substantially straight shape so that when bending forces are imparted to the segments, the inherent restoring forces of the material itself tend to straighten the segments to their straight or unbent position when the bending forces have been removed. The deployment mandrel 26 is used to impart such bending forces counteracting the segments' inherent restoring forces. The mandrel 26 has axial rigidity so that it can not only be pulled but also pushed to control the deployment of the expandable electrode array 18 at the distal end 16 of the body member 14. Pulling the mandrel 26 deploys the array 18 and pushing the mandrel collapses the array.

Referring now additionally to FIGS. 2 and 3, the distal tip of the deployment mandrel 26 is attached to the proximal end of the tip electrode 24. Proximal movement of the deployment mandrel 26 will cause the tip electrode to be moved proximally. Because it is mounted on the array segments 20, the segments are forced to move out of the way of the tip electrode. They do so by bending outwardly as shown in FIGS. 2 and 3. The tip electrode can then be pulled into contact with a stop surface 94 at the distal end 16 of the body member 14 of the catheter and into the deployed/expanded position. This creates the planar array of electrodes 22 shown in FIGS. 2 and 3.

Moving the mandrel 26 distally has the opposite effect. The tip electrode 24 is moved distally as are the array segments 20 connected to the electrode 24 and they collapse onto the body member 14 in the straight shape shown in FIG. 1.

The body member deflection control device 30 is also disposed within the catheter body member 14 and has its distal end attached at the distal end 16 of the body member. The deflection control device preferably comprises a deflection control line 30 having a lubricous coating or jacket (not shown). Pulling the deflection control line 30 will cause a deflection of the distal end 16 of the catheter body member 14. The body member 14 is fabricated of a flexible, resilient material constructed in substantially a straight shape so that when a bending force is imparted to the body member, an opposing straightening or restoring force originating from the body member itself tends to oppose the bending force. When the bending forces have been removed, the inherent material straightening forces tend to return the body member to its straight shape. The deflection control line 30 is used to impart such deflection forces to overcome the body member's restoring force and hold the distal end in a deflected position.

The distal tip of the deflection line 30 is affixed by brazing, soldering, or similar means to an anchor band 32 (FIG. 3) mounted in the distal end 16 of the catheter body member 14. The control line is disposed within another lumen formed in the catheter body member 14 so as to be off-set from the central longitudinal axis Of the catheter body member to more easily effect the controlled deflection of the flexible distal end 16.

When the expandable electrode array 18 is in its collapsed state, as shown in FIG. 1, sliding movements of the control element 28 operate on the deflection control line 30 to result in selective deflection of the catheter distal end for steering the body member 14. The catheter may be steered so that the body member carrying the electrode array 18 may be positioned at desired locations in a patient's intracardial volume of the heart. Once within the intracardial volume of the heart, the electrode array may be deployed, and the deflection control line 30 controlled to allow the physician to adjust the deflection of the distal end 16 of the catheter 10 for placement of the electrodes against target tissue. The electrodes 22 as well as the tip electrode 24 may be used both for mapping and ablation.

The deployment mandrel 26 and the deflection control line 30 are preferably formed of a stainless steel suitable for in vivo use, although other materials may be used. The deflection line 30 in one embodiment was about 0.127 to about 0.254 mm (0.005 to 0.010 inch) in diameter and the deployment mandrel 26 was about 0.254 to about 0.508 mm (0.010 to 0.020 inch) in diameter, and the lengths thereof are appropriate for the catheter in which they are utilized. The above sizes would be adjusted for catheters of different sizes.

Referring now to FIGS. 4 and 5, the expandable electrode array 18 preferably includes four peripheral segments 20. For purposes of illustration and clarity, only two segments are shown. Briefly and in general terms, each of the segments 20 includes a flexible resilient, electrically conductive metallic core member 34 encapsulated in a polymeric electrically insulative casing 36. Each of the respective segments is formed with distal, medial, and proximal pre-formed hinge portions, 38, 40 and 42 respectively, such that when the deployment mandrel 26 is retracted, the segments 20 bend at predetermined places and in predetermined orientations at the respective hinge portions to result in the electrodes 22 expanding outwardly to a predetermined configuration.

Referring now to FIGS. 6 through 12, the method of manufacturing the expandable electrode array 18, and the construction of the electrode array itself will be described in detail. To manufacture the expandable electrode array, a thin sheet of electrically conductive resilient material (not shown), of a thickness on the order of 0.05 mm (0.002 in.) is selected. In the preferred embodiment, the sheet is composed of a nickel-titanium alloy that provides desired flexibility, resilience, strength, and electrical conductivity. In the alternative, stainless steel may be utilized. The sheet is produced using photo-lithography, photo-etching, or other techniques to provide the configuration shown in FIG. 6. As shown, the sheet exhibits a generally square peripheral frame 44 having a generally cruciform blank 46 attached within it, the legs thereof forming the respective core member 34 of each array segment 20, each core member having an inner and an outer end 48 and 50 respectively.

Figure 7:
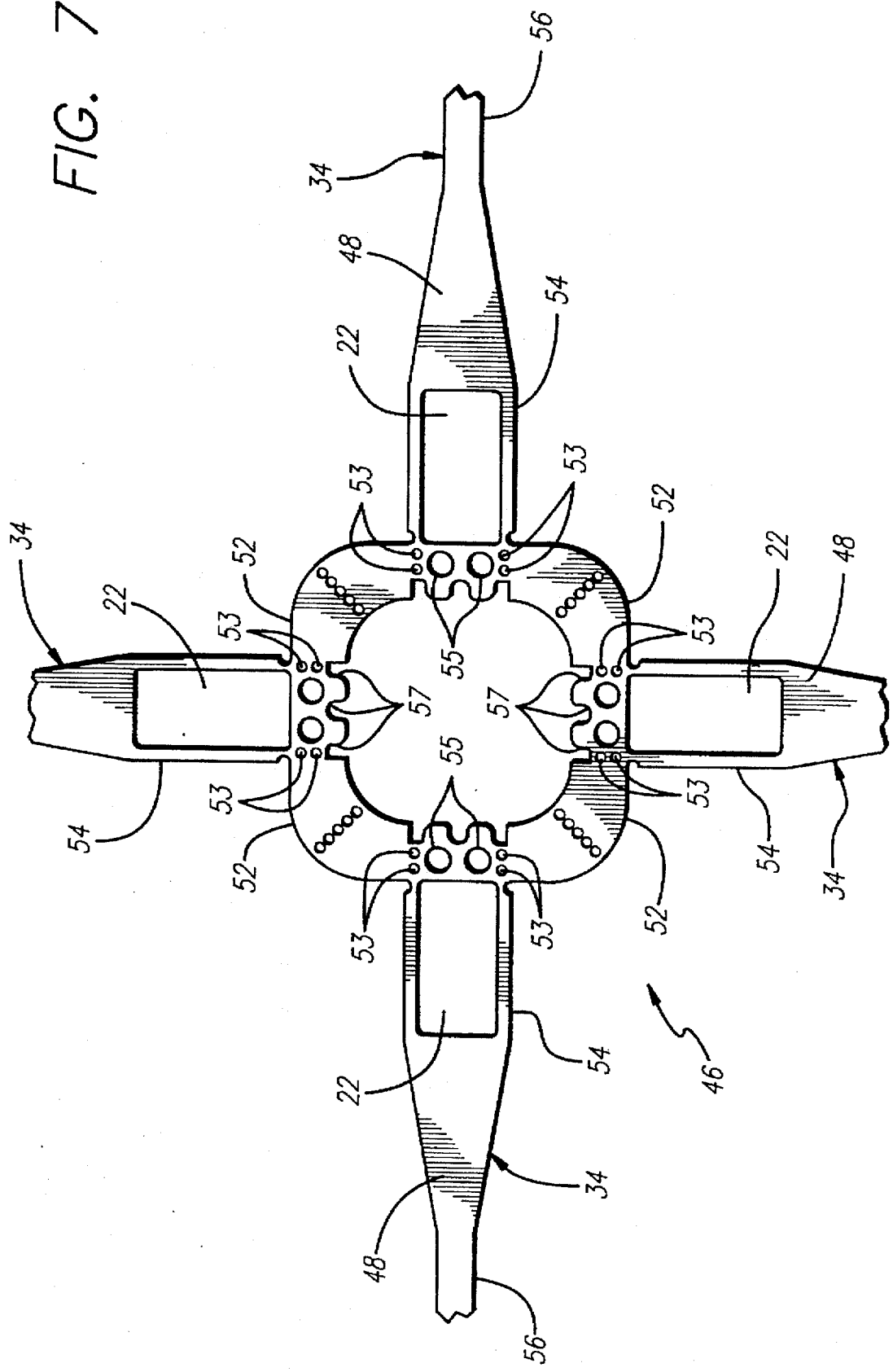
FIG. 7 is an enlarged broken view of a portion of the core members of the array shown in FIG. 6.

Referring more particularly to FIG. 7, the respective inner ends 48 of the respective core members 34 are attached together by right angle tabs 52 having perforations 53 used later in removing the tabs at designated points. The tabs provide spacing between the inner ends of the core members and provide structural integrity to the blank 46 during the manufacturing process. The inner ends of the core members are spaced a predetermined distance apart.

At the inner extremity of the respective core members 34, the core member is relatively wide forming a generally rectangular mounting pad 54. The mounting pads are joined together by the respective tabs 52. Each core member convergingly tapers outwardly from the mounting pad to an elongated lead portion 56. Relatively thin metallic electrodes 22 are affixed to each of the mounting pads 54 of the respective core members 34 by welding, soldering, brazing, or other means, to provide electrical continuity between the electrodes and the core members. In one embodiment, the electrodes 22 comprise highly conductive gold, but may comprise platinum or a platinum alloy in the alternative.

Referring to FIG. 8, the bottom side of the blank 46 is shown in which the core members 34 have been encapsulated in a polymeric casing 36 utilizing injection molding or over-molding processes known well to those skilled in the art. The casing material is electrically insulative. The casings 36 are of uniform width along the length of the respective core members. The central portion of the blank 46, between the inner ends 48 of the core members 34, is molded and filled with polymeric material to form a generally square central electrode mounting plate 64, the mounting plate formed with a central axial through bore 66.

The blank 46 is trimmed from the frame 44 at the respective outer ends 50 (FIGS. 6 and 7), and the respective tabs 52 are trimmed from the inner ends 48 of the respective core members 34 to form the generally cruciform configuration shown in FIG. 8, the legs thereof defining the segments 20 of the expandable electrode array 18. Because the tabs 52 were broken away, none of the respective core members 34 are in electrical contact with any other so that the core members are electrically isolated from one another. The surface of the electrodes 22 may then be cleaned or ground to assure that no polymeric material remains over them. In addition, the electrodes 22 may be ground to assure a smooth finish so that no sharp edges exist that may cause trauma to tissues.

With particular reference to FIG. 9, the mounting plate 64 is relatively thin with respect to the thickness of the casings 36 of the segments 20. In addition, the bottom surface at the inner ends 48 of the respective casings are formed with clearance tapers 68, tapering upwardly and inwardly to the mounting plate to avoid any interference when the segments are bent to the shape shown in FIG. 4.

As illustrated in FIGS. 8 and 9, the bottom sides of the respective casings 36 are formed with a plurality of transverse slots. The slots in one embodiment are molded into the plastic and located at selected distances along the length of the respective segments 20. The slots provide predetermined bending areas or hinges at which the array will bend when deployed or collapsed, depending on the hinge. A first transverse slot 70 defining the distal hinge portion 38 is located at the bottom surface of each casing 36, at the inner end 48 thereof, and inside of the inner extremities of the core members 34 and generally at the periphery of the central mounting plate 64. Spaced a predetermined distance outwardly from the first transverse slot are a plurality of adjacent second transverse slots 72 defining the medial hinge portion 40. In one embodiment, the number of second slots 72 comprising the medial hinge portion is six, however more or fewer slots may be used depending on the arc of curvature desired. Spaced a predetermined distance outwardly from the outward-most slot of the set of second transverse slots is a third transverse slot 74 defining the proximal hinge portion 42.

With particular reference to FIGS. 10 through 11, the cross sectional configuration of the respective segments 20 is described in detail. As shown, the cross section of each of the respective casings 36 of the segments 20 is generally in the form of a circular quadrant having a rounded upper surface 76 and downwardly converging side walls 78. The bottom of the casing is formed with a inwardly rounded bottom surface 80 concentric with the rounded upper surface. The electrodes 22 have a generally rectangular cross-sectional shape with smooth rounded corners at the upper surface. As shown in FIG. 10, the planar upper surface of the electrode is positioned in a tangential orientation relative to the upper rounded surface 76 of the casing such that the rounded corners of the electrode project from the casing to a minor degree. Alternatively, as shown in FIG. 10A, the electrodes may be formed or ground down to have a rounded contoured upper surface, shaped in conformity with the rounded upper surface 76 of the respective segments. The contoured surface eliminates the protrusion of any surface beyond the rounded upper surface 76 of the respective segments such that when the array is in its collapsed state, a smoother surface and smaller profile exist.

As shown in FIG. 11, a transverse slot 72 of the casing 36 traverses the bottom portion of the casing, but does not disturb the integrity of the casing's encapsulation of the core member 34. For further details concerning an electro array, see the co-pending application entitled "Catheter With Expandable Probe" by Jung, Jr. et al., having docket no. 36199 filed the same day, incorporated herein by reference.

Returning to FIGS. 4 and 5, the catheter body member 14 and the mounting and assembly of the expandable electrode array 18 onto the distal end 16 thereof is described hereinafter in detail. As shown, the catheter body member 14 includes an inner lumen 82 formed along the central axis thereof extending the length of the body member and the distal extremity of the catheter body member is formed with a tapered countersink 84.

With particular reference to FIG. 4, the distal tip electrode 24 is generally of a bullet shape having a hemispherical nose. The proximal end of the tip electrode 24 includes a projecting mounting stem 86 having an axial bore 88 for receipt of the distal tip of the deployment mandrel 26, the mandrel being affixed therein by crimping, soldering, brazing or other means. When assembled, the stem of the tip electrode 24 is passed through the central bore 66 of the mounting plate 64 so that the stem and mandrel project proximally from the bottom side thereof. A retaining hub 90 is slid over the proximal end of the mandrel and adhesively bonded to the mounting stem sandwiching the mounting plate 66 between the back surface of the tip electrode and the retaining hub 90 to securely affix the tip electrode mounting plate of the expandable array 18. In an alternative embodiment, the tip electrode 24 may be formed with a peripheral slot, held within the frame 44 (FIG. 6), and the polymeric casing molded around it to engage the peripheral slot thereby holding the tip electrode 24 in a fixed position.

A first tubular sheath 92 is provided having a predetermined length and outer diameter, the distal tip thereof defining a stop surface 94. The first sheath 92 has an inner diameter sized for slidable receipt of the deployment mandrel 26. Because the first sheath 92 and the mandrel 26 are coaxial, the stop surface is in confronting relationship with the retaining hub 90 of the tip electrode 24. A pair of small-diameter sealing O-rings 96 having an inner diameter sized for snug receipt of the mandrel are mounted over the mandrel to abut the proximal end of the first sheath and prevent the passage of fluids.

A flexible elongated second tubular sheath 98 is provided proximal to the first sheath 92 and has a similar outer diameter as the first sheath 92. Furthermore, it has a length substantially the length of the catheter body member 14. The outer diameter of the second sheath is sized for receipt within the inner lumen 82 of the body member 14 and the inner diameter sized for sliding receipt of the mandrel 26. The second sheath is mounted over the mandrel 26 to abut the O rings 96. The distal extremity of the first sheath is a predetermined distance from the retaining hub 90 of the tip electrode 24. The second sheath is composed of PTFE which provides sufficient lubricity such that the mandrel may slide therein without undue frictional constraint. The first sheath is composed of polyimide which provides sufficient rigidity to resist buckling when confronting the retaining hub during deployments of the array.

When the expandable electrode array 18 is assembled, the first sheath 92, O-rings 96 and second sheath 98 are spaced on the deployment mandrel 26 a predetermined proximal distance from the proximal surface of the mounting plate 66. The plastic molding at the proximal and inside portions of the legs 36 is stripped off to expose the underlying electrical conductor 34. Electrical leads are attached to the inside surfaces of the legs and the legs are folded closed over a spacing mandrel (not shown). The legs are then all heat melted together, or an appropriate adhesive may be applied to connect them together permanently in the shape provided by the spacing mandrel between the third slots 74 and the outer ends 50 thereof (FIG. 8). The segments are then heat melted to the distal end of the second sheath 98, the O rings 96, and the proximal end of the first sheath 92. In the alternative, an adhesive may be applied to bond the fused segments to the first and second sheaths 92 and 98 respectively. However, the distal portion of the first sheath 92, distal to the third slot 74, is not bonded to the respective outer ends of the segments. As shown, the clearance tapers 98 of the respective segments provide clearance for the retaining hub 90 of the tip electrode 24 when the array is in its collapsed state. Also, the segments 20 clear the first sheath 92 because of their inwardly rounded bottom surfaces 80 (FIG. 10).

The array is hot melted to the distal end of the body member 14 in order to attach it. In one embodiment, a section of similar material can be used as a filler 100 within the joint section.

As shown in FIGS. 1 and 4, when the electrode array is in its collapsed state, the diameter of the array is substantially the same diameter as the outer diameter of the catheter body member 14. The deployment mandrel 26 is free to slide within the first and second sheaths 92 and 98 to expand and collapse the electrode array 18, while the O-rings 96 seal the mandrel so that bodily fluids do not enter the inner lumen 82 of the body member 14.

Referring to FIG. 5, the deployment mandrel 26 may be pulled proximally relative to the distal end 16 of the body member 14, whereby the distal tip of the mandrel pulls the tip electrode 24 in the proximal direction. As shown, the peripheral segments 20 bend at the distal 38, medial 40, and proximal hinge portions 42. The gradual bending at the roedial hinge portion 40 due to a plurality of slots 72 prevents the conductive core member 34 from being bent too sharply or at an angle such that the encapsulated core member could break disrupting electrical continuity to the electrode 22. The portions of the segments between the distal and roedial hinge portions resist bending due to the relative large width of the mounting pads 48 and the rigidity of the electrodes 22 mounted thereon. The proximal hinge portions 42 bend along the third transverse slots 74 relatively easy with limited bending resistance because the polymeric material of the casing is relatively thin.

With continued reference to FIG. 5, the deployment mandrel 26 may be pulled proximally far enough such that the retaining hub 90 of the tip electrode 24 contacts the stop surface 94 at the distal end of the first sheath 92. The stop surface is positioned at a predetermined distance from the retaining hub in the collapsed configuration such that when the retaining hub contacts the stop surface, the forward portions of the respective segments 20 move radially outwardly about the hinge to an extent where the forward portions are disposed in a generally transverse planar orientation relative to one another. When the forward portions are at such orientation, the electrodes 22 are oriented so that they are all forward facing. When in such configuration, the electrodes may more effectively sense electrical signals emanating from the endocardium of the heart and more effectively make contact with the heart tissue to apply ablation energy. Electrical signals are conducted by the respective conductive core members 34 and through the sensor leads (not shown) disposed within the inner lumen 82 of the body member 14 and to a connector (not shown) mounted in the manipulation handle 12. The external electrical connector 18 (FIG. 1) is connected to signal analysis equipment which provide electrical signal data indications to the physician as well as ablation energy.

The stop surface 94 prevents the deployment mandrel 26 from being retracted within the sheaths 92 and 98 any further which in turn assures that the array 18 is deployed in its predetermined planar orientation while preventing the array from being over-deployed. Deployment of the array at an orientation other than the predetermined orientation may cause irregular electrode sensing characteristics. In addition, over-deployment may cause damage to the internal components of the electrode array.

With particular reference to FIGS. 13, 14 and 15, the manipulation handle 12 will be described in greater detail. The handle 12 includes a handle body 110 formed with an elongated hollow cylindrical sleeve 112 having a partition wall 114 near the proximal end thereof and a contoured cap 116 affixed to proximal end of the handle body. The contoured cap 116 includes an electrical connector 118 (not shown).

The partition wall 116 of the handle body 110 is formed with an axial bore 120 therethrough for receipt of a tubular shaft 122 having an inner lumen 124 and a longitudinal slot 126 extending along the length thereof. The shaft, near the proximal end thereof, has a peripheral groove for receiving a spring clip 128, the proximal extremity of the shaft being threaded. The proximal end of the shaft is received within the bore 120 of the partition wall 114 so that the threaded extremity projects rearwardly therefrom. A nut 130 is thereafter threaded onto the proximal end of the shaft to sandwich the partition wall between the spring clip 128 and the nut anchoring the shaft to the handle body concentrically within the hollow sleeve 112 thereof. In addition, a thread adhesive or a lock washer may be used to hold the nut in place.

An elongated generally hollow nut element 132 is provided having a longitudinal through bore 134. The bore is formed with a pair of radially outwardly opposed helical grooves 136 along its longitudinal length. The distal end of the nut element abuts a generally cylindrical bushing 138 formed with a circumferential locking device groove 140 for housing an annular locking device 142. The bushing is formed with an axial bore 144 therethrough sized for receipt of the tubular shaft 122 and freely rotates about the shaft.

A tubular spacer 146 is provided having an inner diameter sized for disposition over the tubular shaft 122 and an outer diameter sized for receipt within the bore 134 of the nut element 132.

The nut element 132, tubular spacer 146 and bushing 138 are disposed over the tubular shaft 122 concentrically within the sleeve 112 of the handle body 110 so that the end of the nut element, opposite the bushing, abuts the spring clip 128 at the proximal end of the handle body 110. A nut element locking spring clip 148 is positioned over the shaft 122 and that abuts the bushing to restrain the nut element from longitudinal movement, while allowing rotational freedom thereof. The nut element 132 acts as a nut and is rotatable with respect to the handle body 110.

The nut element 132 is provided with a plurality of longitudinally extending guide tracks 150 on the exterior thereof which are adapted to slidably receive respective longitudinal splines 152 disposed on the interior surface of the control element 28, described in more detail below.

A hollow screw element 154 is received within bore 134 of the nut element 132 and includes a pair of opposed projecting helical ridges 155 sized for complementary threaded engagement within the nut element grooves 136. As shown in FIGS. 17 and 18, the screw element includes an inward radial projection 156 or tang. The screw element is disposed over the shaft 122 and the inward projection 156 of the screw element is received within the longitudinal slot 126 of the shaft so that rotation of the screw element is constrained, while longitudinal movement of the screw element relative to the shaft and handle body 110 is provided.

As shown in FIG. 13, the deployment mandrel 26 is passed proximally through the inner lumen 126 of the shaft 122 and is operatively mounted at its proximal end to the inward projection 156 on the screw element 154. The displacement control device 157 transmits control movements from the control element 28 to the deployment mandrel 26.

A distally converging tapered cap 158 having a barbed tubular reinforcing sleeve 160 pressed into proximal end of the cap is slidably disposed over the distal end of the tubular shaft 122 and securely affixed thereto. The distal end of the cap is formed with an axial catheter body member bore 162. The proximal end of the catheter body member 14 is received in the bore 162 and affixed to the cap by suitable adhesive.

The electrical leads (not shown) from the electrodes 22 at the expandable electrode array 18 at the distal end of the catheter body member 14, pass through the inner lumen 124 of the tubular shaft 122, and are electrically connected to the electrical connector (not shown) at the proximal end of the handle 12.

The control element 28 is constructed in two pieces and includes a generally tubular distal sleeve element 164 and a tubular proximal sleeve element 166, the proximal sleeve element having an axial bore 168 therethrough. The axial bore 168 of the proximal sleeve element is sized for slidable receipt of the nut element 132 therein and the outer diameters of the respective sleeve elements are sized for slidable receipt within the hollow sleeve 112 of the handle body 110. The distal end of the distal sleeve element 164 is formed with a knob 170 configured for convenient grasping by the physician. The proximal extremity of the distal sleeve element is formed with an inner annular groove that defines a retention channel 172. The distal end of the proximal sleeve element and the proximal end of the distal sleeve element are joined together to capture a periphery of a pulley ring 174 within the retention channel 172 forming a substantially continuous cylindrical slide element, wherein the ring is free to rotate within the channel without undue frictional counter force acting on the ring.

With reference to FIGS. 5, 16 and 17, the displacement control device 157 that cooperates with the screw element 154 to affect control movements of the deployment mandrel 26 is described in more detail. The displacement control device 157 includes an elongated metallic tube 176 having an inner lumen, and a pair of biasing members 184 and 188 mounted on the tube. As shown in FIG. 16, the inward projection 156 of the screw element 154 is formed with an axial bore 178 therethrough sized for slidable receipt of the metallic tube 176. The inner diameter of the lumen of the metallic tube is sized for receipt of the proximal end of the deployment mandrel 26. As shown, the proximal end of the mandrel 26 is disposed within the inner lumen of the metallic tube and the proximal extremity of the mandrel is affixed to the proximal extremity of the metallic tube, for instance, by crimping, soldering or brazing. An electrically conductive jumper wire 180 is affixed to the proximal extremity of the metallic tube, such as by soldering or brazing, such that the mandrel is in electrical contact with the jumper wire. The jumper wire is then connected to the electrical connector (not shown) at the proximal end of the handle 12.

A rear stop ring 182 is disposed a predetermined distance from the proximal end of the metallic tube and affixed thereto by solder or adhesive. A first helical coil spring 184 comprises one of the biasing members and is disposed over the metallic tube between the stop ring and the screw element 154. An eyelet 186 is slidably mounted over the metallic tube between the first spring 184 and the screw element 154 and is free to slide along the metallic tube. A second helical coil spring 188, of a smaller size than the first spring, comprises a second biasing member and has an inner diameter sized so that it fits over the metallic tube. The second spring 188 is slidably mounted over the distal end of the metallic tube such that the first and second springs are disposed on opposite sides of the inward projection of the screw element 154. A length of shrink tubing 90 in this embodiment is disposed over the distal end of the metallic tube and shrunk about the metallic tube such that the shrink tubing is affixed on the tube and restricts the second spring 188 to remain between it and the screw element 154.

With particular reference to FIGS. 12 and 13, the operation and control of the expandable electrode array will be described in detail. To control the deployment mandrel 26, the slide element 28 is rotated relative to the handle body 110. This causes rotation of a nut element 12 which causes linear movement of the screw element 154. Because the inward projection 156 of the screw element 154 is received within the slot 126 of the shaft 122 and therefore constrained from rotation movement relative thereto, the screw element 154 moves only longitudinally along the tubular shaft 122.

As shown in FIG. 12, the control element 28 has been rotated such that the screw element 154 is disposed in the distal end of the nut element 132. In this position, the deployment mandrel 26 has been pushed distally and has caused the electrode array 18 to collapse as shown in FIG. 1. To avoid excess pressure being placed against the tip electrode 24 by the mandrel 26, the second spring 188 comes into operation. The second spring provides a buffer between the movement of the screw element 154 and the movement of the mandrel. Should the mandrel have reached its most distal position, as controlled by the complete collapse of the array 18, but the control element 28 continues to be rotated to move in the distal direction and become "over-rotated", the second spring 188 will compress thereby storing the excess rotational energy of the control element 28. Therefore the over-rotation of the control element 28 will not place undue mechanical strain on the array elements, which may have included stretching or breakage.

Additionally, the second spring 188 biases the mandrel in the distal direction. This can be particularly useful in the case where the control device was rotated to its distal position to collapse the array while the distal end of the catheter was deflected. When the catheter becomes straightened, the array may tend to partially deploy as described in the Background section. However, the biasing effect of the second spring automatically moves the mandrel more distally keeping the array collapsed.

To deploy and expand the electrode array 18, the control element 28 is rotated so that it moves proximally relative to the handle body 110 such that the screw element 154 is moved in the proximal direction within the nut element 132, as shown in FIG. 13. Because the deployment mandrel 26 is connected to the metallic tube 176 and the first spring 184 is disposed between the rear stop ring 182 and the proximal end of the inward projection 156 of the screw element 154, longitudinal proximal movement of the screw element compresses the first spring. The compressed first spring 184 induces a spring force to the stop ring 182 to move the metallic tube in a proximal direction resulting in longitudinal movement of the deployment mandrel 26 within the catheter body member 14. As is shown, a gap exists between the second spring 188 and the screw element 154.

Thus, the deployment mandrel 26 pulls the tip electrode 24 proximally to flare the respective segments 20 radially outwardly, as shown in FIG. 2, wherein the retaining hub 90 abuts the stop surface 94 of the array. The control element 28 is further rotated such that the screw element 154 moves proximally a further distance so that the screw element 154 abuts the tubular spacer 146, at the proximal end of the nut element 132. This further compression of the first spring 184, applies a continuous spring force to the mandrel, such that the retaining hub 90 of the tip electrode 24 abuts the stop surface 94 of the first sheath 92 with a continuous contact force. This contact force maintains the retaining hub in contact with the stop surface so that the electrode array maintains its predetermined, fully deployed configuration even in the case where the distal end of the catheter is deflected.

Referring to FIGS. 12, 13, and 14, the operation of the deflection control device of the catheter 10 is described in detail. The deflection of the distal end is controlled by the control element 28 that slides to achieve such deflections. As shown in FIG. 12, the control element 28 has been slid to its distal position wherein the control line applies no tensile force to the distal end 16 of the body member and thus the catheter would be disposed in its undetected state as shown in FIG. 1.

As shown in FIG. 13, the control element 28 has been slid to its proximal position. With the control element in this position, the control line has exerted tension on the distal end 16 of the catheter body member 14 deflecting it as shown in FIG. 3. For further details of a deflection control system, see the co-pending application entitled "Catheter Control System Having A Pulley" by Thornton et al., filed this same day having docket no. 36203.

Once the distal end deflection of the body member 14 has been selected, the clinician may release the control element 28, and it will remain in the position selected due to the inclusion in the handle of a locking device. The locking device 142 in this embodiment exerts an outward radial force to impart a continuous locking force against the control element bore 168 sufficient to resist the tensile force of the deflection control line 30. For further details on a locking device incorporating the above feature, see the patent application filed the same day as this application entitled "Locking Mechanism For Catheters" to Iain Smith and incorporated herein by reference.

While the invention has been described herein in terms of certain embodiments, it is clear that those embodiments are susceptible to numerous modifications and adaptations within the ability of those skilled in the art and without the exercise of inventive faculty. Thus, it should be understood that various changes in form, detail and usage of the present invention may be made without departing from the spirit and scope of the invention.

What is claimed is:

1. A catheter comprising:

a resilient body member having a distal end and a proximal end;

a manipulation handle attached to the proximal end of the body member and including a linearly movable first element;

a mandrel having proximal and distal ends mounted in the body member; and a biasing member interconnecting the proximal end of the mandrel with the first element to bias the mandrel in a predetermined direction in relation to the first element and such that linear movement of the first element is transmitted to the mandrel through the biasing member to cause the mandrel to move linearly in response to the linear movement of the first element.

2. The catheter of claim 1 further comprising:

a tip electrode mounted at the distal tip of the body member;

wherein the mandrel is electrically conductive and the handle and first element are electrically insulative, the distal end of the mandrel connected to the tip electrode.

3. The catheter of claim 1 further including;

a movable device mounted at the distal end of the body member and mounted to the mandrel so that the movement of the device is controlled by the movement of the mandrel;

a stop surface mounted at the distal end of the body member and located a predetermined distance from the movable device such that movement of the moveable device is limited by the stop surface;

wherein once the mandrel has been moved to place the movable device in contact with the stop surface, the biasing member applies a continuous biasing force on the mandrel to hold the movable device against the stop surface.

4. The catheter of claim 3 wherein the biasing member comprises a helical coil spring mounted between the mandrel and the first element and is in compression when the movable device is against the stop surface.

5. The catheter of claim 3 wherein:

the biasing member comprises a first and a second biasing device;

the movable device has a first stop position at the stop surface and a second stop position;

once the mandrel has been moved to place the movable device in contact with the stop surface, the biasing member applies a continuous biasing force on the mandrel to hold the movable device against the stop surface; and once the mandrel has been moved to place the movable device at the second stop position, the second biasing device applies a continuous biasing force on the mandrel to hold the movable device against the second stop.

6. The catheter of claim 1 wherein the biasing member comprises a pair of springs having first and second ends, the springs disposed on opposite sides of the first element such that the first ends of the respective springs are in confronting alignment with the first element and the second ends of the respective springs are mounted to the mandrel.

7. The catheter of claim 6 wherein the two springs are slidably disposed over the mandrel and the mandrel is formed with a pair of spaced apart fixed stop rings, disposed on opposite sides of the first element, against which the second ends of the respective springs abut.

8. A catheter comprising:

a longitudinally compressible resilient body member having a distal end and a proximal end;

a manipulation handle attached to the proximal end of the body member having a first movable control element;

an energy transfer device mounted at the distal end of the catheter such that it has a deployed configuration and a non-deployed configuration;

a mandrel having proximal and distal ends mounted in the body member and mounted to the energy transfer device such that movement of the mandrel controls the deployment configuration of the energy transfer device;

a displacement compensation device including a spring member interconnecting the proximal end of the mandrel with the first element such that movement of the first element is transmitted to the mandrel through the spring member to cause the mandrel to move in response to said linear movement of the first element thereby controlling the deployment configuration of the energy transfer device.

9. The catheter of claim 8 wherein:

the spring member also biases the mandrel in a selected direction thereby biasing the energy transfer device into a selected deployment configuration.

10. The catheter of claim 8 wherein the energy transfer device comprises an expandable electrode array.

11. A catheter comprising:

a resilient body member having a distal end and a proximal end;

a manipulation handle attached to the proximal end of the body member and including a linearly movable first element;

a mandrel having proximal and distal ends mounted in the body member;

a biasing member having first and second biasing devices, the biasing member interconnecting the proximal end of the mandrel with the first element to bias the mandrel in a predetermined direction in relation to the first element such that linear movement of the first element is transmitted to the mandrel through the biasing member to cause the mandrel to move linearly in response to the linear movement of the first element;

a movable device mounted at the distal end of the body member and mounted to the distal end of the mandrel so that movement of the device is controlled by the movement of the mandrel;

a stop surface mounted at the distal end of the body member and located a predetermined distance from the movable device such that movement of the moveable device is limited by the stop surface such that the movable device has a first stop position at the stop surface and a second stop position; wherein once the mandrel has been moved to place the movable device in contact with the stop surface, the biasing member applies a continuous biasing force on the mandrel to hold the movable device against the stop surface; and once the mandrel has been moved to place the movable device at the second stop position, the second biasing device applies a continuous biasing force on the mandrel to hold the movable device against the second stop position.

12. The catheter of claim 11 wherein the moveable device comprises an energy transfer device.

13. The catheter of claim 12 wherein the energy transfer device comprises an array of electrodes having a deployed configuration and a non-deployed configuration.

14. A catheter comprising:

a resilient body member having a distal end and a proximal end;

a manipulation handle attached to the proximal end of the body member having a first movable control element;

a mandrel having proximal and distal ends mounted in the body member; and a displacement compensation device including a first spring member interconnecting the proximal end of the mandrel with the first element such that movement of the first movable control element is transmitted to the mandrel through the first spring member to cause the mandrel to move in response to linear movement of the first movable control element.

15. The catheter of claim 14 further comprising:

a movable device mounted at the distal end of the catheter having a deployed and a non-deployed configuration and mounted to the mandrel such that movement of the mandrel controls the deployment configuration of the movable device.

16. The catheter of claim 15 further comprising:

a stop surface mounted at the distal end of the body member and located at a predetermined location in relation to the movable device such that movement of the movable device is limited by the stop surface;

wherein once the mandrel has been moved to place the movable device in contact with the stop surface, the displacement compensation device applies a continuous biasing force on the mandrel to hold the movable device against the stop surface.

17. The catheter of claim 16 wherein:

the movable device has a first stop position at the stop surface and a second stop position;

once the mandrel has been moved to place the movable device in contact with the stop surface, the first spring member applies a continuous biasing force on the mandrel to hold the movable device against the stop surface; and once the mandrel has been moved to place the movable device at the second stop position, the second spring member applies a continuous biasing force on the mandrel to hold the movable device in the second stop position.

18. The catheter of claim 15 wherein the movable device comprises an energy delivery device.

19. The catheter of claim 18 wherein the energy delivery device comprises an expandable array having a collapsed configuration in a non-deployed configuration and an expanded configuration in a deployed configuration.

20. The catheter of claim 14 wherein the displacement compensation device further comprises a second spring member interconnecting the proximal end of the mandrel with the first element, the first and second spring members each having first and second ends, the spring members disposed on opposite sides of the first movable control element such that the first ends of the respective springs are in confronting alignment with the first movable control element and the second ends of the respective springs are mounted to the mandrel.

21. The catheter of claim 20 wherein the first and second spring members are slidably disposed over the mandrel and the mandrel is formed with a pair of spaced apart fixed stop rings, disposed on opposite sides of the first movable control element, against which the second ends of the first and second spring members abut.

22. The catheter of claim 21 further comprising:

a movable device mounted at the distal end of the catheter having a deployed and a non-deployed configuration and mounted to the mandrel such that movement of the mandrel controls the deployment configuration of the movable device;

a stop surface mounted at the distal end of the body member and located at a predetermined location in relation to the movable device such that movement of the movable device is limited by the stop surface;

wherein the movable device has a first stop position at the stop surface and a second stop position;

once the mandrel has been moved to place the movable device in contact with the stop surface, the first spring member applies a continuous biasing force on the mandrel to hold the movable device against the stop surface; and once the mandrel has been moved to place the movable device at the second stop position, the second spring member applies a continuous biasing force on the mandrel to hold the movable device in the second stop position.

* * * * *